(12) United States Patent
Redel

(10) Patent No.: US 7,610,081 B2
(45) Date of Patent: Oct. 27, 2009

(54) METHOD AND DEVICE FOR GENERATING AN IMAGE USING OPTICAL COHERENCE TOMOGRAPHY

(75) Inventor: Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 252 days.

(21) Appl. No.: 11/484,197

(22) Filed: Jul. 11, 2006

(65) Prior Publication Data

US 2007/0015979 A1    Jan. 18, 2007

(30) Foreign Application Priority Data

Jul. 14, 2005    (DE) .................. 10 2005 032 961

(51) Int. Cl.
*A61B 6/00*    (2006.01)
(52) U.S. Cl. ........................ 600/473; 600/476
(58) Field of Classification Search ............... 600/103, 600/117, 118, 310, 315, 316, 341, 342, 476–478; 385/115
See application file for complete search history.

(56) References Cited

U.S. PATENT DOCUMENTS

| | | | |
|---|---|---|---|
| 4,998,972 A * | 3/1991 | Chin et al. | 600/109 |
| 5,178,616 A * | 1/1993 | Uemiya et al. | 606/7 |
| 6,134,003 A * | 10/2000 | Tearney et al. | 356/479 |
| 6,485,413 B1 * | 11/2002 | Boppart et al. | 600/160 |
| 6,615,071 B1 * | 9/2003 | Casscells et al. | 600/474 |
| 7,376,455 B2 * | 5/2008 | Crowley et al. | 600/473 |
| 2004/0092830 A1 * | 5/2004 | Scott et al. | 600/478 |
| 2005/0085769 A1 * | 4/2005 | MacMahon et al. | 604/96.01 |

FOREIGN PATENT DOCUMENTS

| | | |
|---|---|---|
| EP | 0 330 376 A2 | 8/1989 |
| WO | WO 97/32182 A1 | 9/1997 |
| WO | WO 2004/012589 A2 | 2/2004 |
| WO | WO 2004/096317 A2 | 11/2004 |

\* cited by examiner

*Primary Examiner*—Eric F Winakur

(57) ABSTRACT

The invention relates to a method for generating an image using optical coherence tomography, with a control device controlling the operation of an image generation device and a rinsing device automatically according to a predetermined program.

16 Claims, 1 Drawing Sheet

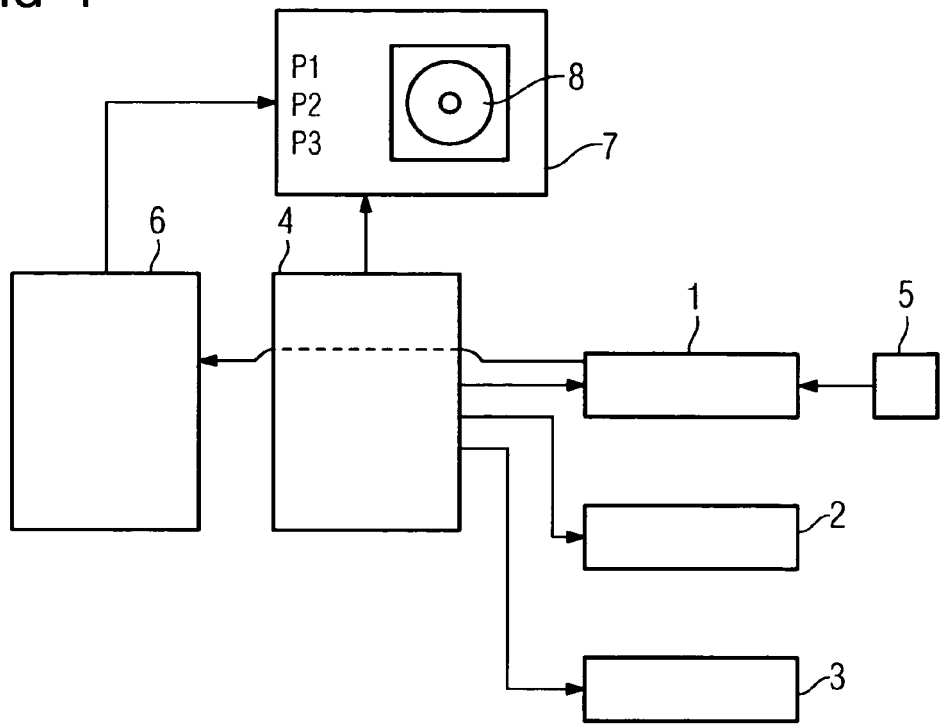
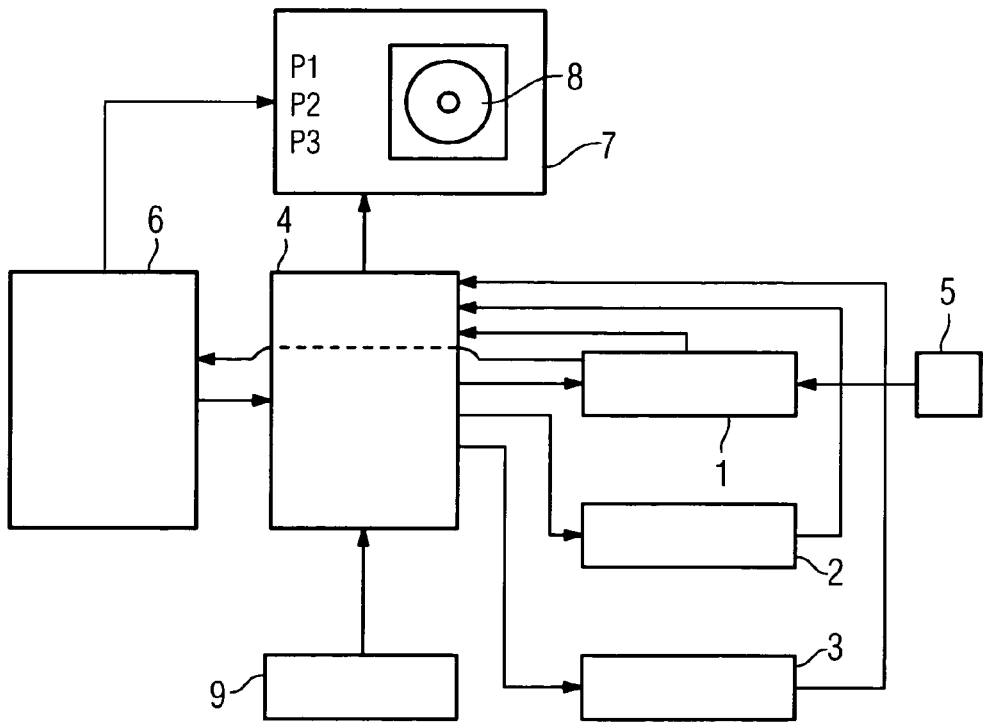

is part of the heart for example, the required sealing or occlusion of the vessel can cause

METHOD AND DEVICE FOR GENERATING AN IMAGE USING OPTICAL COHERENCE TOMOGRAPHY

CROSS REFERENCE TO RELATED APPLICATIONS

This application claims priority of German application No. 10 2005 032 961.6 filed Jul. 14, 2005, which is incorporated by reference herein in its entirety.

FIELD OF THE INVENTION

The invention relates to a method and device for generating an image using optical coherence tomography.

BACKGROUND OF THE INVENTION

Optical coherence tomography (OCT) is an optical method, with which images can be produced from inside vessels. Such a method is known from example from WO 97/32182 A1.

To produce images, a catheter is inserted into the vessel. At the tip of the catheter, rotating about a catheter axis, light in the light wave range of around 1,300 nm is emitted onto the surrounding vessel wall. The light reflected in the region of the vessel wall is detected and evaluated using interferometry. As a result it is possible to produce a two-dimensional image, which provides information about the vessel wall with depth resolution. If the catheter is also displaced in the vessel parallel to the catheter axis, a number of such two-dimensional images can be recorded in a continuous manner. A three-dimensional image can be generated from the number of two-dimensional images.

However the production of images using OCT requires that the blood contained in the section of the vessel to be examined is removed therefrom. To this end the vessel can be sealed using a balloon provided on the catheter or on a further catheter. Such a catheter is for example known from EP 0 330 376 A2. When the vessel has been sealed, the blood contained therein is displaced by means of a rinsing fluid, which is delivered into the vessel by the catheter or the further catheter. A separate injection device is provided to deliver the rinsing fluid.

If the vessel to be examined is part of the heart for example, the required sealing or occlusion of the vessel can cause cardiac activity to be disrupted. It is therefore necessary to seal the vessel to be examined for as short a time period as possible.

According to the prior art, separate devices have to be operated by the treating doctor and their assistants to carry out an examination using OCT. The balloon is generally inflated manually using a pump. An injector or fluid pump has to be operated to deliver the rinsing fluid. A displacement device has to be operated to rotate the OCT catheter and/or displace it in an axial manner. Operation of the above-mentioned separate devices requires team coordination and skill. If the devices are not operated in an optimum manner, the time period for which the vessel is occluded has to be extended in an undesirable manner.

SUMMARY OF THE INVENTION

The object of the invention is to eliminate the disadvantages according to the prior art. In particular a method and device are to be specified, which simplify and accelerate an examination using OCT.

This object is achieved by the features of the independent claims. Expedient developments of the invention will emerge from the features of the dependent claims.

According to the invention a method is provided for generating an image using OCT with the following steps:

Provision of a catheter with a transmitter/receiver for transmitting and receiving light and an image generation device for generating an image, from the light received with the receiver, Provision of a rinsing device for delivering rinsing fluid into a section of a vessel containing the transmitter/receiver according to a predetermined program, and Provision of a control device for controlling the image generation device and the rinsing device, such that when the image generation device is switched on, the rinsing device is switched on at the same time and rinsing fluid is delivered at a predetermined rate.

According to the proposed method the operation of the image generation and rinsing devices is controlled automatically using a control device according to a predetermined program. This simplifies and accelerates an examination using OCT. It is no longer necessary for a number of people to operate a number of separate devices manually. It is possible in particular to avoid the time loss that results if the rinsing device is not switched on at the right time during the examination.

The rinsing device expediently delivers rinsing fluid for a predetermined time period and/or a predetermined quantity of rinsing fluid. The time period or quantity can be set such that the blood is displaced safely and reliably from the section of the vessel to be examined, thereby ensuring the production of perfect images using OCT. The time period and/or quantity can be set in the program.

According to an advantageous development the control device also controls an occlusion device for the optional sealing of the vessel according to the predetermined program. This allows the operational process for generating an image using OCT to be fully automated. The method is thereby significantly simplified and accelerated.

The occlusion device can be controlled with the control device such that rinsing fluid is delivered before the vessel is sealed with the occlusion device. This allows the blood to be displaced at least partially from the section of the vessel to be examined, before the vessel is sealed. The occlusion period can be further reduced as a result.

According to a further development of the invention the control device also controls a displacement device to displace the catheter in the direction of a catheter axis and/or to rotate the catheter about its axis according to the predetermined program. The proposed development further increases the degree of automation of the method.

The displacement device is advantageously controlled such that displacement of the catheter in the direction of the catheter axis only takes place, when rinsing fluid is delivered using the rinsing device. Displacement of the catheter in the direction of the catheter axis to generate a three-dimensional image is then only possible according to the claimed method, when the vessel is rinsed. This prevents unintended premature operation of the displacement device and an undesirable extension of the time required for the OCT examination.

According to a further development the control device interrupts the delivery of rinsing fluid, when displacement in the direction of the catheter axis is terminated. Interruption of the delivery of rinsing fluid can also take place with a time delay according to program parameters. Termination of displacement can be effected manually or automatically according to the predetermined program. The proposed method step prevents the patient being subjected to unnecessary stress due to rinsing with rinsing fluid.

An operating state of the displacement device, rinsing device and optionally the occlusion device is advantageously displayed on a display device. The display device is expediently a monitor, for example an LCD flat screen. In this way the treating doctor can identify the state of proceedings at a glance during the production of an image using OCT. The images currently being generated can also be displayed on the display device in addition to the operating states of the displacement device, the rinsing device and optionally the occlusion device. Because according to the invention the method operates in a partially or fully automatic manner using the control device, the doctor can concentrate on the image information supplied and can optionally detect medically relevant information more readily.

Provision is expediently made for a pressure required to activate the occlusion device to be regulated using a regulator which forms part of the control device. The occlusion device generally comprises an inflatable balloon. The pressure required to inflate the balloon can be regulated according to the predetermined program for example such that a predetermined maximum pressure is not exceeded. This makes it possible to prevent excessive pressure being exerted on the vessel wall. The pressure can in particular be regulated such that it remains constant. This ensures reliable sealing of the vessel during the examination.

The proposed regulator can also be used to detect and analyze image information supplied. It is then possible for example for the displacement device for displacing the catheter in the direction of the catheter axis only to be operated when adequate image quality is identified by the regulator. One parameter for judging image quality may for example be the achievement of a predetermined contrast.

A device for generating an image using optical coherence tomography (OCT) is further provided according to the invention, comprising A catheter with a transmitter/receiver for transmitting and receiving light, An image generation device for generating an image from the light received with the receiver, A rinsing device for delivering rinsing fluid into a section of a vessel containing the transmitter/receiver according to a predetermined program and A control device for controlling the image generation device and the rinsing device such that when the image generation device is switched on, the rinsing device is switched on at the same time and rinsing fluid can be delivered at a predetermined rate.

The control device proposed according to the invention allows the method to be implemented in an at least partially automated manner during the production of images using OCT.

According to an advantageous development of the invention the control device can also control an occlusion device for the optional sealing of a vessel according to the predetermined program. The occlusion device can be controlled with the control device such that rinsing fluid is delivered before the vessel is sealed with the occlusion device.

According to a further development a displacement device is provided to displace the catheter in the direction of a catheter axis and/or to rotate the catheter about its axis. The displacement device can be controlled with the control device according to the predetermined program such that displacement of the catheter in the direction of the catheter axis only takes place when rinsing fluid is delivered using the rinsing device. Displacement of the catheter in the direction of the catheter axis is thus only possible when there is sufficient rinsing fluid in the vessel and perfect image generation is thus possible.

According to an advantageous development the rinsing device can deliver rinsing fluid for a predetermined time period and/or a predetermined quantity of rinsing fluid before displacement of the catheter. The time period and/or quantity can be set such that generation of a three-dimensional image only takes place when the blood, which interferes with image generation, has been displaced completely out of the vessel.

The control device expediently comprises a process computer. Suitable interfaces can also be provided on the control device to connect the displacement device, the rinsing device and optionally the occlusion device. The interfaces are configured such that a conventional displacement device, rinsing device and optionally also a conventional occlusion device can be connected thereto. The control device is expediently a correspondingly set-up computer, on which the control program is provided. The program is configured in particular such that it can be used to set the parameters of relevance for control purposes.

According to a further development of the invention the device comprises the rinsing device and/or the occlusion device. The device can also comprise a display device to display the operating state of the displacement device, the rinsing device and optionally the occlusion device. A device with the above-mentioned development features represents an integrated system, with which the method can be implemented in a fully automated manner during the production of images using OCT.

Further advantageous development features of the device will emerge from the developments described in relation to the method, which can also be applied analogically to the device.

BRIEF DESCRIPTION OF THE DRAWINGS

Exemplary embodiments of the invention are described in more detail based on the drawings, in which:

FIG. 1 shows a schematic diagram of the essential components of a first device and FIG. 2 shows a schematic diagram of the essential components of a second device.

DETAILED DESCRIPTION OF THE INVENTION

FIGS. 1 and 2 show a displacement device 1, a fluid pump 2 and a pressure generator 3 connected to a control device 4.

A catheter 5 is connected to the displacement device 1. The catheter 5 can be rotated about its axis and can also optionally be displaced in the direction of the catheter axis using the displacement device 1. Image signals supplied by the catheter 5 are detected by the displacement device 1, then expediently-digitized and transmitted to an OCT device 6. Conversion of the image signals to an image 8 that can be displayed using the display device 7 takes place in the OCT device 6. The reference signs P1, P2, P3 refer to parameters, which show an operating state of the displacement device, the fluid pump 2 and the pressure generator 3.

The fluid pump 2 is used to deliver rinsing fluid. It can be connected to the catheter 5 and optionally also to a further catheter (not shown here) via a hose for delivering rinsing fluid. The rinsing fluid can in particular be a fluid, the refractive index of which is suitable for components of the blood. Such a fluid is characterized by a particularly high light range in the blood.

The pressure generator 3 is used to inflate a balloon provided on the catheter 5 or optionally on a further catheter (not shown here) with fluid. The balloon serves to occlude the vessel to be examined. The pressure generator 3 can be a pump. Such a pressure generator 3 expediently comprises a throttle valve that can be controlled or regulated.

The functions of the devices are as follows:

In the case of the device shown in FIG. 1, the control device, which is expediently a computer, controls, in other words in particular switches on and off, the displacement device 1, the fluid pump 2 and the pressure generator 3 according to a predetermined program. The following method can for example be implemented using the program:

Start of the method,

Switching on of the fluid pump 2,

Switching on of the pressure generator 3 and inflation of the balloon, during which process a maximum pressure may not be exceeded, Displacement of the catheter 5 in the direction of the catheter axis, Termination of the displacement of the catheter 5 in the direction of the catheter axis, and Switching off of the fluid pump 2 and deflation of the balloon.

The above method steps can be carried out one after the other at predetermined time intervals. It is also possible to set the length of a path, along which the catheter 5 is displaced. The current operating state of the displacement device 1, the fluid pump 2 and the pressure generator 3 can be displayed together with the image 8 as parameters P1, P2, P3 on the display device 7.

In the case of the second device shown in FIG. 2, the control device 4 also comprises a regulator. This makes is possible to control and/or regulate the displacement device 1, the fluid pump 2 and the pressure generator 3 as a function of predetermined parameters and/or measured values. It is in particular possible only to start the displacement device 1, when a predetermined minimum image contrast has been achieved. To this end the catheter 5 is continuously rotated using the displacement device 1. A two-dimensional image is produced from the image data obtained using the OCT device 6. With a further program the OCT device 6 can also be used to determine the contrast of the image produced. The contrast values can be transmitted to the control device 4. When a predetermined contrast value is achieved, the program can activate the displacement device 1 such that the catheter 5 is displaced in the direction of the catheter axis.

The delivery output of the fluid pump 2 can similarly be regulated as a function of the observed image quality. For example the quantity of rinsing fluid delivered can always be such that a predetermined image quality is achieved.

A pressure generated by the pressure generator 3 can be measured using a pressure sensor and be maintained at a predetermined value by means of suitable regulation. This ensures that the balloon is not subject to impermissibly high pressure or to a pressure that is too low.

The proposed control device 4 can also be connected to an electrocardiography device 9. Such an electrocardiography device 9 can be used to monitor the cardiac activity of the patient. If the electrocardiography device 9 transmits a signal indicating cardiac malfunction to the control device 4, the balloon can be deflated automatically, thereby eliminating the occlusion of the vessel.

The invention claimed is:

1. A method for generating an image using optical coherence tomography in a medical procedure, comprising:
    transmitting and receiving light with a transmitter and a receiver arranged on a catheter;
    generating an image from the light received by an image generation device using the optical coherence tomography;
    delivering a rinsing fluid into a section of a vessel of a patient containing the transmitter and receiver using a rinsing device;
    sealing the vessel with an occlusion device; and
    automatically controlling an operation of the image generation device and the rinsing device, and the occlusion device using a control device according to a predetermined program, wherein the control device controls a displacement device to displace the catheter in a direction of an axis of the catheter or to rotate the catheter with the axis when the rinsing fluid is delivered.

2. The method as claimed in claim 1, wherein the operation is controlled so that the image generation device and the rinsing device are switched on simultaneously and the rinsing fluid is delivered at a predetermined rate.

3. The method as claimed in claim 2, wherein the rinsing device delivers the rinsing fluid for a predetermined time period or a predetermined quantity.

4. The method as claimed in claim 1, wherein the control device controls an occlusion device for sealing the vessel and controls the rinsing device to deliver the rinsing fluid before the vessel is sealed.

5. The method as claimed in claim 4, wherein the control device comprises a regulator which regulates a pressure required for activating the occlusion device.

6. The method as claimed in claim 4, wherein an operating state of the occlusion device is displayed on a display device.

7. The method as claimed in claim 1, wherein the control device interrupts the delivery of the rinsing fluid when the displacement is terminated.

8. The method as claimed in claim 1, wherein an operating state of the displacement device and the rinsing device is displayed on a display device.

9. A device for generating an image using optical coherence tomography in a medical procedure, comprising:
    a catheter with a transmitter and a receiver for transmitting and receiving light;
    an image generation device for generating an image from the light received using the optical coherence tomography;
    a rinsing device for delivering a rinsing fluid into a section of a vessel of a patient containing the transmitter and the receiver;
    an occlusion device for sealing the vessel,
    a displacement device for displacing the catheter in a direction of an axis of the catheter or to rotate the catheter with the axis, and
    a control device operatively connected to the image generation device, the rinsing device, displacement device, and occlusion device for automatically controlling an operation of the image generation device and the rinsing device, displacement device, and the occlusion device, wherein the control device controls the displacement device to displace the catheter when the rinsing fluid is delivered.

10. The device as claimed in claim 9, wherein the control device controls the operation so that the image generation device and the rinsing device are switched on simultaneously and the rinsing fluid is delivered at a predetermined rate.

11. The device as claimed in claim 9, wherein the control device controls an occlusion device for sealing the vessel and controls the rinsing device to deliver the rinsing fluid before the vessel is sealed.

12. The device as claimed in claim 11, wherein the control device comprises a regulator to regulate a pressure which is required to activate the occlusion device.

13. The device as claimed in claim 9, wherein the rinsing device delivers the rinsing fluid for a predetermined time period or a predetermined quantity before the displacement of the catheter.

14. The device as claimed in claim 9, wherein the control device interrupts the delivery of the rinsing fluid when the displacement is terminated.

15. The device as claimed in claim 9, wherein the control device comprises a processing computer.

16. The device as claimed in claim 9, wherein the device comprises a display device to display an operating state of the rinsing device, a displacement device, and the occlusion device.

* * * * *

UNITED STATES PATENT AND TRADEMARK OFFICE
CERTIFICATE OF CORRECTION

PATENT NO.      : 7,610,081 B2                           Page 1 of 1
APPLICATION NO. : 11/484197
DATED           : October 27, 2009
INVENTOR(S)     : Thomas Redel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 360 days.

Signed and Sealed this

Twelfth Day of October, 2010

David J. Kappos
*Director of the United States Patent and Trademark Office*